(12) United States Patent
Knebel

(10) Patent No.: US 8,916,724 B2
(45) Date of Patent: Dec. 23, 2014

(54) METHOD FOR THE PRODUCTION OF (METH)ACRYLIC ESTERS

(75) Inventor: Joachim Knebel, Alsbach-Haehnlein (DE)

(73) Assignee: Evonik Roehm GmbH, Darmstadt (DE)

( * ) Notice: Subject to any disclaimer, the term of this patent is extended or adjusted under 35 U.S.C. 154(b) by 417 days.

(21) Appl. No.: 12/990,095

(22) PCT Filed: May 5, 2009

(86) PCT No.: PCT/EP2009/055367
§ 371 (c)(1),
(2), (4) Date: Oct. 28, 2010

(87) PCT Pub. No.: WO2010/003709
PCT Pub. Date: Jan. 14, 2010

(65) Prior Publication Data
US 2011/0130590 A1    Jun. 2, 2011

(30) Foreign Application Priority Data

Jul. 7, 2008 (DE) .................. 10 2008 040 221

(51) Int. Cl.
*C07C 67/03* (2006.01)
(52) U.S. Cl.
CPC .................... *C07C 67/03* (2013.01)
USPC ....................................... 560/217
(58) Field of Classification Search
CPC ...................................... C07C 67/03
USPC ....................................... 560/217
See application file for complete search history.

(56) References Cited

U.S. PATENT DOCUMENTS

| 3,488,321 A | * | 1/1970 | Stark et al. ............ 528/106 |
| 4,091,225 A | * | 5/1978 | Parker .................... 560/20 |
| 4,276,195 A | * | 6/1981 | Verkade ................. 502/155 |
| 4,299,922 A | | 11/1981 | Hoell et al. |
| 5,407,506 A | | 4/1995 | Goetz et al. |
| 6,008,371 A | | 12/1999 | Knebel et al. |
| 7,862,885 B2 | | 1/2011 | Tong |
| 2005/0119500 A1 | * | 6/2005 | Ackermann et al. ..... 560/217 |
| 2007/0123673 A1 | | 5/2007 | Hofer et al. |
| 2010/0204509 A1 | | 8/2010 | Protzmann et al. |

FOREIGN PATENT DOCUMENTS

| GB | 1 094 998 | 12/1967 |
| GB | 1 401 843 | 7/1975 |
| GB | 2 037 608 | 7/1980 |
| JP | 62-218495 | 9/1987 |
| JP | 2001-321675 | 11/2001 |
| JP | 2003-321420 | 11/2003 |
| JP | 2007-516240 | 6/2007 |
| JP | 2008-37847 | 2/2008 |
| TW | 200728273 | 8/2007 |

OTHER PUBLICATIONS

International Search Report issued Feb. 9, 2010 in PCT/EP09/55367 filed May 5, 2009.
Office Action issued May 17, 2011, in Israeli Patent Application No. 205212 (with English-language translation).
Office Action issued Aug. 26, 2013, in Japanese Patent Application No. 2011-517047, filed May 5, 2009.
Combined Taiwanese Office Action and Search Report issued Feb. 13, 2014 in Patent Application No. 098122409 with English Translation.

* cited by examiner

*Primary Examiner* — Yevegeny Valenrod

(74) *Attorney, Agent, or Firm* — Oblon, Spivak, McClelland, Maier & Neustadt, L.L.P.

(57) ABSTRACT

The present invention relates to a process for preparing (meth)acrylates, comprising the transesterification of a low-boiling ester of (meth)acrylic acid with a reactant alcohol in the presence of catalysts, which is characterized in that the transesterification is catalysed by a basic ion exchanger.

21 Claims, No Drawings

METHOD FOR THE PRODUCTION OF (METH)ACRYLIC ESTERS

The present invention relates to processes for preparing (meth)acrylic esters.

(Meth)acrylic esters are widely known and frequently used monomers. Accordingly, various methods of obtaining these compounds are known. To prepare specialty (meth)acrylates, transesterification reactions are frequently carried out, in which methyl (meth)acrylate is reacted with an appropriate alcohol. To improve the yield and the selectivity of the reaction, different catalysts have been used to date.

For example, publication DE 28 05 702 describes the preparation of esters of unsaturated carboxylic acids. For the catalysis of the reactions described, it is possible to use especially compounds which contain zirconium and/or calcium. The particularly suitable catalysts include especially zirconium acetylacetonate. The reactions lead to high yields of approx. 97%, based on the alcohol used.

In addition, it is possible to use acids or bases in order to catalyse the transesterification. Such reactions are detailed, for example, in CN 1355161, DE 34 23 443 or EP-A-0 534 666. The basic catalysts include especially lithium amide, as detailed, by way of example, in publications DE 34 23 443, CA 795814 and U.S. Pat. No. 6,194,530.

In addition, it has been proposed to improve the economic viability of the preparation by adding the starting compounds in the course of the reaction. For example, publication U.S. Pat. No. 5,072,027 describes addition of alcohol and methyl methacrylate after a high conversion of the starting compounds used at the start of the reaction.

The reactions detailed above already lead to a high conversion and to pure products. Owing to the high economic significance of specialty (meth)acrylates, however, there is a permanent drive to further improve the preparation of these compounds.

One disadvantage of the processes detailed above is that the catalysts have to be removed from the reaction mixtures. The removal irreversibly alters many of the catalysts detailed above, such that they cannot be reused.

In view of the prior art, it was thus an object of the present invention to provide a process for preparing (meth)acrylates, in which the product can be obtained in a very economically viable manner. In addition, the (meth)acrylic ester obtained should contain only very small amounts of by-products and catalyst residues.

It was a further object of the invention to provide a process in which (meth)acrylates can be obtained very selectively.

It was a further object of the present invention to provide processes for preparing (meth)acrylates which can be carried out simply and inexpensively. At the same time, the product should as far as possible be obtained in high yields and, viewed overall, with low energy consumption.

In addition, a process should be provided which can be carried out without complicated removal of the catalyst.

These objects and further objects which are not stated explicitly but which are immediately derivable or discernible from the connections discussed herein by way of introduction are achieved by processes having all features of claim 1. Appropriate modifications to the processes according to the invention are protected in the dependent claims referring back to claim 1.

The present invention accordingly provides a process for preparing (meth)acrylates, comprising the transesterification of a low-boiling ester of (meth)acrylic acid with a reactant alcohol in the presence of catalysts, which is characterized in that the transesterification is catalysed by a basic ion exchanger.

It is thus possible in an unforeseeable manner to provide a process for preparing (meth)acrylates, in which the product is obtained in a very economically viable manner. Surprisingly, the product obtained contains only very small amounts of by-products and catalyst residues. The catalyst for use in accordance with the invention can be removed in a particularly simple and complete manner. The catalyst can be reused without any great complexity.

In addition, the process according to the invention enables a particularly selective preparation of (meth)acrylates.

Furthermore, the process according to the invention can be carried out simply and inexpensively, the product being obtainable in high yields and, viewed overall, with low energy consumption. In addition, the process according to the invention can be carried out continuously in a particularly simple manner. This allows a high product quality to be obtained at very low cost.

According to the invention (meth)acrylates are prepared, the expression "(meth)acrylate" representing methacrylic esters, acrylic esters and mixtures of the two. (Meth)acrylates are widely known per se. These compounds include (meth)acrylates which derive from saturated alcohols, such as hexyl (meth)acrylate, 2-ethylhexyl (meth)acrylate, heptyl (meth)acrylate, 2-(tert-butylamino)ethyl (meth)acrylate, octyl (meth)acrylate, 3-isopropylheptyl (meth)acrylate, nonyl (meth)acrylate, decyl (meth)acrylate, undecyl (meth)acrylate, 5-methylundecyl (meth)acrylate, dodecyl (meth)acrylate, 2-methyldodecyl (meth)acrylate, tridecyl (meth)acrylate, 5-methyltridecyl (meth)acrylate, tetradecyl (meth)acrylate, pentadecyl (meth)acrylate, hexadecyl (meth)acrylate, 2-methylhexadecyl (meth)acrylate, heptadecyl (meth)acrylate, 5-isopropylheptadecyl (meth)acrylate, 4-tert-butyloctadecyl (meth)acrylate, 5-ethyloctadecyl (meth)acrylate, 3-isopropyloctadecyl (meth)acrylate, octadecyl (meth)acrylate, nonadecyl (meth)acrylate, eicosyl (meth)acrylate, cetyleicosyl (meth)acrylate, stearyleicosyl (meth)acrylate, docosyl (meth)acrylate and/or eicosyltetratriacontyl (meth)acrylate;

(meth)acrylates which derive from unsaturated alcohols, for example 2-propynyl (meth)acrylate, allyl (meth)acrylate, vinyl (meth)acrylate, oleyl (meth)acrylate;

cycloalkyl (meth)acrylates such as cyclopentyl (meth)acrylate, 3-vinylcyclohexyl (meth)acrylate, cyclohexyl (meth)acrylate, bornyl (meth)acrylate;

(meth)acrylates which have two or more (meth)acryloyl groups, glycol di(meth)acrylates, such as ethylene glycol di(meth)acrylate, diethylene glycol di(meth)acrylate, triethylene glycol di(meth)acrylate, tetra- and polyethylene glycol di(meth)acrylate, 1,3-butanediol (meth)acrylate, 1,4-butanediol (meth)acrylate, 1,6-hexanediol di(meth)acrylate, glyceryl di(meth)acrylate and dimethacrylates of ethoxylated bisphenol A;

(meth)acrylates with three or more double bonds, for example glyceryl tri(meth)acrylate, trimethylolpropane tri(meth)acrylate, pentaerythrityl tetra(meth)acrylate and dipentaerythrityl penta(meth)acrylate.

The particularly preferred (meth)acrylates include especially 2-ethylhexyl methacrylate, ethylene glycol dimethacrylate (2-methylpropenoic acid 1,2-ethanediyldiester; CAS number 97-90-5), ethoxylated bisphenol A dimethacrylate, 1,3-butanediol dimethacrylate (CAS number 1189-08-8), 1,4-butanediol dimethacrylate (CAS number 2082-81-7) and/or trimethylolpropane trimethacrylate.

To prepare the (meth)acrylates, according to the invention, an alcohol is used, which is also referred to herein as reactant alcohol. The type of alcohol is determined here by the intended target compound. Accordingly, it is possible to use especially alcohols having 5 or more carbon atoms, unsaturated alcohols and/or polyhydric alcohols. The preferred alcohols having 5 or more carbon atoms include, for example, pentanol, hexanol, 2-ethylhexanol, heptanol, 2-tert-butylheptanol, octanol, 3-isopropylheptanol, nonanol, decanol, undecanol, 5-methylundecanol, dodecanol, 2-methyldodecanol, tridecanol, 5-methyltridecanol, tetradecanol, pentadecanol, hexadecanol, 2-methylhexadecanol, heptadecanol, 5-isopropylheptadecanol, 4-tert-butyloctadecanol, 5-ethyloctadecanol, 3-isopropyloctadecanol, octadecanol, nonadecanol, eicosanol, cetyleicosanol, stearyleicosanol, docosanol and/or eicosyltetratriacontanol. The preferred unsaturated alcohols include especially 2-propyn-1-ol, allyl alcohol and vinyl alcohol, and/or oleyl alcohol.

In a particular aspect of the present invention, it is possible to use monohydric alcohols which comprise exactly one hydroxyl group.

Particular preference is given to using polyhydric alcohols. Polyhydric alcohols are organic compounds having two, three, four or more hydroxyl groups. These compounds include especially ethylene glycol, trimethylolpropane, 1,2-propanediol, 1,3-propanediol, 1,3-butanediol, 1,4-butanediol, ethoxylated bisphenol A, 1,6-hexanediol, pentaerythritol, polyethylene glycol, especially polyethylene glycol 400, and/or glycerol, particular preference being given to trimethylolpropane. The compounds are in many cases commercially available, for example, from BASF AG, Celanese AG or Clariant GmbH.

According to the present invention, an alcohol is reacted with a low-boiling ester of (meth)acrylic acid. The term "low-boiling ester" means that the ester used as the starting compound has a lower boiling point than the ester obtained by the transesterification. At a pressure of 10 mbar, the difference in boiling point is preferably at least 2° C., more preferably at least 10° C. and most preferably at least 20° C. Particularly suitable (meth)acrylates are formed especially by alcohols having from 1 to 4 carbon atoms. These include especially methanol, ethanol, n-propanol, isopropanol, n-butanol and tert-butanol. Particular preference is given to using especially ethyl (meth)acrylate or methyl (meth)acrylate, very particular preference being given to methyl methacrylate.

The weight ratio of reactant alcohol to the low-boiling ester of (meth)acrylic acid is preferably in the range from 2:1 to 1:20, more preferably 1:2 to 1:15 and most preferably in the range from 1:3 to 1:10.

The inventive transesterification is catalysed by a basic ion exchanger. The basic ion exchangers for this purpose are widely known per se, and are described in detail, for example, in Ullmanns Encyclopedia of Industrial Chemistry (6$^{th}$ edition).

Basic ion exchangers preferably have a polymeric skeleton which has been modified with basic groups. The preferred polymeric skeletons include especially polymers based on styrene and poly(meth)acrylates, these polymers more preferably being crosslinked. This crosslinking can be effected, for example, with divinylstyrene. In addition, it is possible to use phenol-formaldehyde resins or polyalkylamine resins. The preferred basic groups include especially groups comprising nitrogen, which may be aliphatic or aromatic.

For example, basic ion exchangers in the active form may comprise ammonium groups and/or pyridinium groups. Preferred amino groups correspond generally to the formula $P—V—NR_3^+$ in which P is the polymeric skeleton, V is a bond or a connecting group and R is independently hydrogen or an alkyl group having 1 to 4 carbon atoms. The preferred alkyl groups include especially the methyl group and the ethyl group. The connecting group may be a group having 1 to 100, preferably 1 to 4, carbon atoms. V is preferably a bond, or a methylene, ethylene, propylene or butylene group.

The transesterification reaction can preferably be carried out with a strongly basic ion exchanger. Strongly basic ion exchangers include a quaternary nitrogen group, i.e. the nitrogen atom does not have a bond to a hydrogen atom. Accordingly, strongly basic ion exchangers include, for example, pyridinium groups alkylated on the nitrogen or quaternary ammonium groups, where, for example, all R radicals in formula $P—V—NR_3^+$ denote a group having preferably 1 to 4 carbon atoms.

Ion exchangers here may also include different nitrogen-containing groups. Accordingly, it is possible to use ion exchangers which have primary, secondary, tertiary and/or quaternary amino groups. These compounds exhibit both properties of strongly basic ion exchangers and of weakly basic ion exchangers.

For the reaction, the ion exchanger is generally converted to a form which, in the event of reaction with water, leads to a rise in the pH, i.e. the ion exchanger is laden with a basic anion so as to obtain a basic ion exchanger. The preferred basic anions include especially hydroxide ions and carbonate ions.

Preferred ion exchangers have, in dried form, a particle size in the range from 0.3 to 0.8 mm, more preferably in the range from 0.5 to 0.7 mm, which is measured by screen analysis.

The exchange capacity of the ion exchangers is not critical per se, and is preferably in the range from 0.5 eq/l to 1.8 eq/l, more preferably in the range from 0.7 eq/l to 1.5 eq/l (dry state).

For reasons of cost and owing to their performance, preference is given especially to basic ion exchangers based on polystyrene which have quaternary amino groups.

The anion exchangers described above are obtainable commercially, inter alia, from Bayer AG under the trade name ®Lewatit; from Rohm & Haas Comp./USA under the trade name ®Amberlite, ®Ambersep and ®Amberlyst, and from The Dow Chemical Com./USA under the trade name ®Dowex. More preferably, it is possible to use especially ®Ambersep 900 and ®Amberlyst A26 for the transesterification.

The amount of catalyst used may be within a wide range. Of particular interest are, however, processes in which the proportion of the catalyst, based on the weight of the reaction partners used, is in the range from 0.1 to 30% by weight, preferably in the range from 1 to 20% by weight and more preferably in the range from 5 to 15% by weight. This weight is based on the dry weight of the ion exchanger used.

The reaction can be effected under elevated or reduced pressure. In a particularly appropriate modification of the present invention, the transesterification can be carried out at a pressure in the range from 200 to 2000 mbar, more preferably in the range from 500 to 1300 mbar.

The reaction temperature may likewise be within a wide range, especially depending on the pressure. In a preferred embodiment of the present invention, the reaction is effected preferably at a temperature in the range from 50° C. to 140° C., more preferably in the range from 70° C. to 120° C. and most preferably 80 to 110° C.

Surprisingly, it is possible to achieve particular advantages if the temperature at which the reaction is effected is increased in the course of reaction. In this preferred modification of the process according to the invention, the temperature at the start of the reaction, especially up to a conversion of 80%, preferably up to a conversion of 70%, based on the weight of the alcohol used, may preferably be in the range from 50° C. to 90° C., and, toward the end of the reaction, especially after a conversion of 80%, preferably after a conversion of 90%, based on the weight of the alcohol used, in the range from 95° C. to 130° C.

It is additionally surprising that, at the aforementioned reaction temperatures, no noticeable deactivation of the ion exchangers occurs. For the preferably strongly basic ion exchangers used especially in the OH form, the manufacturers specify a maximum use temperature which is well below the reaction temperature in the transesterification. For instance, the maximum use temperature according to the data sheet for ®Amberlyst A 26 OH and ®Ambersep 900 OH is 60° C. Above these temperatures, the quaternary ammonium salt structures are supposed to be degraded by amine elimination.

Owing to the surprisingly low deactivation of the catalyst, a basic ion exchanger already used in a transesterification reaction can be used as a catalyst in a further reaction. A spent basic ion exchanger can preferably be regenerated by treating with an aqueous alkali metal hydroxide or carbonate solution.

The process according to the invention can be carried out in bulk, i.e. without use of a further solvent. If desired, it is also possible to use an inert solvent. These include benzene, toluene, n-hexane, cyclohexane and methyl isobutyl ketone (MIBK) and methyl ethyl ketone (MEK).

The transesterification preferably takes place with exclusion of water, though small amounts of water can be tolerated in many cases. According to this aspect of the present invention, the reaction mixture comprises preferably at most 0.5% by weight of water, more preferably at most 0.05% by weight of water.

In a particularly appropriate variant of the inventive transesterification, all components, for example the alcohol, the methacrylic ester and the catalyst, are mixed, and this reaction mixture is then heated to boiling. Subsequently, the alcohol released, for example methanol or ethanol, can be removed from the reaction mixture by distillation, optionally azeotropically with methyl methacrylate or ethyl methacrylate.

The reaction times depend upon factors including the parameters selected, for example pressure and temperature. They are, however, generally in the range from 1 to 24 hours, preferably from 3 to 20 hours and most preferably 4 to 12 hours. In continuous processes, the residence times are generally in the range from 0.5 to 24 hours, preferably from 1 to 12 hours and most preferably 2 to 4 hours. Further information in relation to the reaction times can be taken by the person skilled in the art from the examples adduced.

The reaction can preferably take place with stirring, in which case the stirrer speed may more preferably be in the range from 50 to 2000 rpm, most preferably in the range from 100 to 500 rpm.

The pH may be within a wide range. Appropriately, the reaction can be carried out at a pH in the range from 8 to 14, preferably 9 to 13. To determine the pH, a portion of the reaction mixture can be added to an excess of water (for example 10 times the weight). Subsequently, the pH of the aqueous phase is determined in a conventional manner at 25° C.

In order to prevent undesired polymerization of the methacrylates, polymerization inhibitors can be used in the reaction. These compounds, for example hydroquinones, hydroquinone ethers such as hydroquinone monomethyl ether or di-tert-butylpyro-catechol, phenothiazine, N,N'-(diphenyl)-p-phenylenediamine, 4-hydroxy-2,2,6,6-tetramethylpiperidine 1-oxyl, p-phenylenediamine, methylene blue or sterically hindered phenols, are widely known in the technical field. These compounds can be used individually or in the form of mixtures and are generally commercially available. The effect of the stabilizers is usually that they act as free-radical scavengers for the free radicals which occur in the course of polymerization. For further details, reference is made to the standard technical literature, especially to Römpp-Lexikon Chemie; editors: J. Falbe, M. Regitz; Stuttgart, N.Y.; $10^{th}$ edition (1996); under "Antioxidants" and the references cited in this reference.

Preference is given to using especially phenols as the polymerization inhibitor. Particularly surprising advantages can be achieved in the case of use of hydroquinone monomethyl ether. Based on the weight of the overall reaction mixture, the proportion of the inhibitors, individually or as a mixture, may generally be 0.01-0.5% (wt/wt).

These polymerization inhibitors can be added to the reaction mixture before or at the start of the reaction. In addition, it is also possible to add portions of the polymerization inhibitors added during the transesterification. Of particular interest in this context are especially processes in which a portion of the polymerization inhibitor is added via the column reflux. Particularly appropriate mixtures are, among others, those which comprise methyl methacrylate, hydroquinone monomethyl ether and 4-hydroxy-2,2,6,6-tetramethylpiperidine 1-oxyl. This measure especially allows undesired polymerization within the distillation column to be avoided.

For inhibition, it is additionally possible to use oxygen. In this case, it can be used, for example, in the form of air, in which case the amounts are advantageously metered in such that the content in the gas phase above the reaction mixture remains below the explosion limit. Particular preference is given here to amounts of air in the range from 0.05 to 0.5 l per hour and mole of alcohol. In batchwise processes, this amount may be based on the amount of alcohol originally used. In continuous processes, this amount may be based on the amount of alcohol supplied. It is likewise possible to use inert gas-oxygen mixtures, for example nitrogen-oxygen or argon-oxygen mixtures.

In a particular configuration of the present invention, a combination of oxygen with at least one phenol, preferably hydroquinone monomethyl ether, can be used for inhibition.

The alcohol released from the (meth)acrylate used, for example methanol and/or ethanol, can preferably be removed by distillation. In this case, it is advantageously possible, for example, to remove a mixture which comprises methyl methacrylate and methanol. Surprisingly, a portion of the mixture removed can advantageously be recycled into the next batch. According to this modification, the recyclable proportion of the mixture removed can be obtained toward the end of the reaction, especially after a conversion of 80%, preferably after a conversion of 90%, of the alcohol used. For example, the proportion of the mixture recycled at the start of the next batch may be in the range from 10 to 50%, based on the total initial weight of methacrylic ester to be transesterified.

The transesterification can be carried out either continuously or batchwise. A continuous reaction can preferably be performed in plants with a plurality of reactors, in which case it is possible, inter alia, to alter the reaction temperature and to remove alcohol which is released from the low-boiling (meth) acrylic ester from the reaction system.

Of particular interest are especially semibatchwise processes in which a portion of the reaction mixture is initially charged. In further steps or continuously, low-boiling ester of (meth)acrylic acid can be added to the reaction mixture after the start of the reaction.

In a particular modification of the present invention, the molar ratio of low-boiling ester of (meth)acrylic acid to reactant alcohol present in the reaction mixture can be increased during the reaction by adding low-boiling ester of (meth) acrylic acid. The expression "addition of low-boiling ester" means that this compound is supplied from an external source. A pure reflux which is effected within the distillation column accordingly does not constitute an addition. Of particular interest are especially processes in which the molar ratio of the proportion of low-boiling ester of (meth)acrylic acid to the proportion of the alcohol used for transesterification present in the reaction mixture is increased during the reaction by at least 10%, more preferably by at least 40% and most preferably by at least 100% by adding low-boiling ester of (meth)acrylic acid. For example, the molar ratio of the low-boiling ester added during the reaction to the amount of the low-boiling ester used at the start of the reaction may be in the range from 1:5 to 2:1, more preferably 1:3 to 1:1.5. Appropriately, the weight ratio of reactant alcohol to the low-boiling ester of (meth)acrylic acid at the start of the reaction may preferably be in the range from 1:2 to 1:8, more preferably 1:2.5 to 1:6 and most preferably in the range from 1:3 to 1:4. Addition of low-boiling ester during the reaction allows this ratio to be increased, for example, to from 1:3 to 1:20, preferably 1:4 to 1:15 and most preferably 1:6 to 1:10. These values are always based on the reactant alcohol present in the reaction mixture. The proportion of the reactant alcohol already converted to the product ester can in many cases be determined by the proportion of alcohol released by the reaction which has been distilled off. In addition, the proportion of reactant alcohol present in the reaction mixture can be determined by gas chromatography.

In a particular configuration, the amount of low-boiling ester of (meth)acrylic acid added can be controlled by the amount of alcohol released which is removed from the reaction mixture. For control, it is possible, for example, to use the temperature which is established at a suitable height in the column. It is also possible to adjust the reflux ratio via the temperature in the column during the distillative removal of the alcohol released from the reactant. When, for example, a mixture which comprises methanol and methyl methacrylate is removed from the reaction mixture, a temperature of approx. 75 to 85° C. can be imposed over a prolonged period, above which no distillate is drawn off. Only below this temperature is a corresponding amount of a mixture removed. This can achieve the effect that a relatively high ratio of low-boiling (meth)acrylate to reactant alcohol is maintained over a long period, without excessively great amounts of low-boiling (meth)acrylate having to be supplied to the reaction mixture.

Surprisingly, an addition of low-boiling ester during the transesterification allows particularly high exploitation of the vessel volume to be achieved, such that large amounts of specialty (meth)acrylates can be obtained even with relatively small plants. In addition, the amount of specialty (meth) acrylate obtained per batch can be increased, such that further advantages can be achieved, since the costs of performing the reaction fall, based on the amount of product obtained.

Appropriately, the low-boiling ester of (meth)acrylic acid can be added over a period which corresponds to at least 30%, preferably at least 50% and very particularly at least 70% of the reaction time. In this case, the addition can be effected in steps within this period, the first addition fixing the start of this period and the last addition the end of this period. Preference is given to effecting the addition in at least three, preferably at least 5 and most preferably at least 10 steps. In addition, this addition can also be effected continuously.

Processes of particular interest include batchwise processes in which methyl (meth)acrylate is added during the transesterification. This embodiment is advantageous, for example, if methyl (meth)acrylate is removed from the reaction mixture together with methanol. The weight ratio of the amount of methyl (meth)acrylate added during the transesterification to the amount of methanol-methyl (meth)acrylate mixture removed may preferably be in the range from 2:1 to 1:2, more preferably 1.5:1 to 1:1.5.

In batchwise processes, excess reactant, especially the unconverted ester of (meth)acrylic acid, can be removed by distillation toward the end of the reaction. This too can be reused in the next batch without further purification.

The distillate obtained at the start of the reaction, which may comprise, for example, large amounts of methanol or ethanol, can likewise be recycled, for example by incorporation into a plant operated in an integrated system for preparing the (meth)acrylic ester to be transesterified.

A suitable plant for performing the present transesterification may, for example, comprise a stirred tank reactor with a stirrer unit, steam heating, distillation column and condenser. Such plants are known per se and are described, for example, in Ullmanns Encyclopedia of Industrial Chemistry (6$^{th}$ edition), Verlag Wiley-VCH, Weinheim 2003, Volume 10, page 647. The size of the plant depends on the amount of (meth) acrylate to be prepared, the present process being performable either on laboratory scale or on the industrial scale. In a particular aspect, the stirred tank reactor may accordingly have a tank volume in the range from 1 m$^3$ to 30 m$^3$, preferably 3 m$^3$ to 20 m$^3$. The stirrer unit of the reactor vessel may especially be configured in the form of an anchor stirrer, impeller, paddle stirrer or inter-MIG stirrer.

The task of the distillation column is to ensure that a methanol- or ethanol-rich azeotrope is removed in order to minimize the losses of reactant ester which is inevitably also discharged. The distillation column may possess one, two or more plates. The number of plates refers to the number of trays in a tray column or the number of theoretical plates in the case of a column with structured packing or a column with random packing. Examples of a multistage distillation column with trays include those such as bubble-cap trays, sieve trays, tunnel-cap trays, valve trays, slotted trays, slotted sieve trays, bubble-cap sieve trays, nozzle trays, centrifugal trays, and examples of a multistage distillation column with random packings include those such as Raschig rings, Lessing rings, Pall rings, Berl saddles, Intalox saddles, and examples of a multistage distillation column with structured packings include those such as the Mellapak (Sulzer), Rombopak (Kühni), Montz-Pak (Montz) type. By virtue of the conversion-dependent adjustment of the reflux ratio, it is possible, for example, in the case of use of methyl methacrylate, over wide ranges of the conversion, to establish a methanol content in the distillate which is above 60%.

The suitable condensers which may be present in the plant for performing the present transesterification include plate and tube bundle heat exchangers.

After the reaction has ended, the resulting (meth)acrylate in many cases already satisfies the high demands detailed above, and so a further purification is in many cases unnecessary. For further enhancement of quality and especially catalyst removal, the resulting mixture can be purified by known processes.

In one configuration of the process according to the invention, the resulting product mixture can be purified by filtration processes. These processes are known from the prior art (W. Gösele, Chr. Alt in Ullmann's Encyclopedia of Industrial Chemistry, (6$^{th}$ edition), Verlag Wiley-VCH, Weinheim 2003, Volume 13, pages 731 and 746), and customary filtration assistants, for example bleaching earth and/or aluminium silicate (perlite) can be used. For example, it is possible to use, inter alia, continuously operable filters for a precoat filtration or cartridge filters.

A further improvement in the quality of the product can be achieved, for example, by a distillation of the filtrate obtained. Owing to the polymerization tendency of the monomer, distillation processes in which the thermal stress on the substance to be distilled is minimized are advisable. Very suitable apparatus is that in which the monomer is evaporated continuously from a thin layer, such as falling-film evaporators and evaporators with a rotating wiper system. It is also possible to use short-path evaporators. Such apparatus is known (Ullmanns Encyclopedia of Industrial Chemistry (6$^{th}$ edition), Verlag Wiley-VCH, Weinheim 2003, Volume 36, page 505). For example, it is possible to use a continuous evaporator with a rotating wiper system and attached column. The distillation can be carried out, for example, at a pressure in the range from 1 to 40 mbar and an evaporator temperature of 120° C. to 150° C.

The present invention will be illustrated hereinafter with reference to some examples, without any intention that this should impose a restriction.

EXAMPLE 1

In a 1000 ml four-neck round-bottom flask equipped with a sabre stirrer with a stirrer sleeve and stirrer motor, air inlet, bottom thermometer and a distillation column with a column head and reflux divider, 170 g (1.3 mol) of 2-ethylhexyl alcohol, 455 g (4.55 mol) of methyl methacrylate (MMA), 0.129 g of hydroquinone monomethyl ether and 0.003 g of 4-hydroxy-2,2,6,6-tetramethylpiperidinyl-1-oxyl (inhibitors), and, as a catalyst, 62.5 g (10% by weight) of ®Amberlyst A26 (Rohm & Haas Comp./USA) in the hydroxide form, were mixed. Subsequently, the mixture was stirred at a bottom temperature of 100° C. to 123° C. with introduction of air for 7 hours, in the course of which methanol and methyl methacrylate were distilled off. After the reaction had ended, the product was filtered through a fluted filter to remove the catalyst and freed of MMA at 10 mbar.

The resulting yield of 2-ethylhexyl methacrylate was 117 g (45% based on the 2-ethylhexyl alcohol used). The purity of the product was 92.3% (determined by gas chromatography).

A portion of the product is bound adsorptively by the catalyst, which is appropriately reused in the next batch.

EXAMPLE 2

In a 1000 ml four-neck round-bottom flask equipped with a sabre stirrer with a stirrer sleeve and stirrer motor, air inlet, bottom thermometer and a distillation column with a column head and reflux divider, 606 g (6.06 mol) of methyl methacrylate (MMA), 0.124 g of hydroquinone monomethyl ether and 0.0025 g of 4-hydroxy-2,2,6,6-tetramethylpiperidinyl-1-oxyl (inhibitors), and, as a catalyst, 70.5 g (10% by weight) of ®Amberlyst A26 (Rohm & Haas Comp./USA) in the hydroxide form, were mixed. The mixture was heated to boiling with introduction of air and dewatered azeotropically until a bottom temperature of 98° C. is attained. Subsequently, 99 g (1.1 mol) of 1,4-butanediol and an amount of MMA corresponding to the MMA-water mixture distilled off (240 g) were added. The mixture was then stirred at a bottom temperature of 100° C. to 113° C. with introduction of air for 5 hours, in the course of which methanol and methyl methacrylate were distilled off. After the reaction had ended, the product was filtered through a fluted filter to remove the catalyst and freed of the MMA at 2 mbar.

The resulting yield of 1,4-butanediol dimethacrylate was 133 g (53% based on the alcohol used). The purity of the product was 87.5% (determined by gas chromatography). The product contains 10% polymerizable high boilers, and so the content of reactive product esters is 97.5%.

A portion of the product is bound adsorptively by the catalyst, which is appropriately reused in the next batch.

EXAMPLE 3

In a 1000 ml four-neck round-bottom flask equipped with a sabre stirrer with a stirrer sleeve and stirrer motor, air inlet, bottom thermometer and a distillation column with a column head and reflux divider, 74.5 g (1.2 mol) of ethylene glycol, 600 g (6 mol) of methyl methacrylate (MMA), 0.119 g of hydroquinone monomethyl ether and 0.0024 g of 4-hydroxy-2,2,6,6-tetramethylpiperidinyl-1-oxyl (inhibitors), and, as a catalyst, 67.5 g (10% by weight) of ®Amberlyst A26 (Rohm & Haas Comp./USA) in the hydroxide form, were mixed. Subsequently, the mixture was stirred at a bottom temperature of 100° C. to 121° C. with introduction of air for 5 hours, in the course of which methanol and methyl methacrylate were distilled off. After the reaction had ended, the product was filtered through a fluted filter to remove the catalyst, the catalyst was extracted with 100 g of MMA, and product and extract together were freed of the MMA at 10 mbar.

The resulting yield of ethylene glycol dimethacrylate was 178 g (74.8% based on the ethylene glycol used). The purity of the product was 89.8% (determined by gas chromatography). The product contains 5.7% polymerizable high boilers and 0.47% hydroxyethyl methacrylate, such that the content of reactive product esters is 96%. The Pt-Co colour number is 44.

A portion of the product is bound adsorptively by the catalyst, which is appropriately reused in the next batch.

EXAMPLE 4

In a 1000 ml four-neck round-bottom flask equipped with a sabre stirrer with a stirrer sleeve and stirrer motor, air inlet, bottom thermometer and a distillation column with a column head and reflux divider, 495 g (4.95 mol) of methyl methacrylate (MMA), 0.06 g of phenothiazine and 0.0045 g of 4-hydroxy-2,2,6,6-tetramethylpiperidinyl-1-oxyl (inhibitors), and, as a catalyst, 78.4 g (10% by weight) of ®Amberlyst A26 (Rohm & Haas Comp./USA) in the hydroxide form, were mixed. The mixture was heated to boiling with introduction of air and dewatered azeotropically until a bottom temperature of 98° C. was attained. Subsequently, 285 g (0.9 mol) of Dianol® 220 (diethoxylated bisphenol A from Seppic, France) and an amount of MMA corresponding to the MMA-water mixture distilled off (310 g) were added. The mixture was then stirred at a bottom temperature of 100° C. to 120° C. with introduction of air for 8.5 hours, in the course of which methanol and methyl methacrylate were distilled off. After the reaction had ended, the product was filtered through a fluted filter to remove the catalyst, the catalyst was extracted with 100 g of MMA, and product and extract together were freed of MMA at 3 mbar.

The resulting yield of ethoxylated bisphenol A dimethacrylate was 338 g (83% based on the raw material used). The purity of the product was 83.4% (determined by gas chromatography). The product contains 13.9% polymerizable high boilers, such that the content of reactive product esters is 97.3%. The Pt-Co colour number is 30.

A portion of the product is bound adsorptively by the catalyst, which is appropriately reused in the next batch.

EXAMPLE 5

In a 1000 ml four-neck round-bottom flask equipped with a sabre stirrer with a stirrer sleeve and stirrer motor, air inlet, bottom thermometer and a distillation column with a column head and reflux divider, 285 g (0.9 mol) of Newpol® BPE 20-F (diethoxylated bisphenol A from Sanyo, Japan), 495 g (4.95 mol) of methyl methacrylate (MMA), 0.06 g of phenothiazine and 0.0045 g of 4-hydroxy-2,2,6,6-tetramethylpiperidinyl-1-oxyl (inhibitors), and, as a catalyst, 78.4 g (10% by weight) of used catalyst from Example 4, were mixed. The mixture was then stirred at a bottom temperature of 100° C. to 120° C. with introduction of air for 8 hours, in the course of which methanol and methyl methacrylate were distilled off. After the reaction had ended, the product was filtered through a fluted filter to remove the catalyst, the catalyst was extracted with 100 g of MMA, and product and extract together were freed of the MMA at 3 mbar.

The resulting yield of ethoxylated bisphenol A dimethacrylate was 350 g (86% based on the raw material used). The purity of the product was 70.8% (determined by gas chromatography). The product contains 24.5% polymerizable high boilers, such that the content of reactive product esters is 95.3%. The Pt-Co colour number is 25.

A portion of the product is bound adsorptively by the catalyst, which is appropriately reused in the next batch.

EXAMPLE 6

In a 1000 ml four-neck round-bottom flask equipped with a sabre stirrer with a stirrer sleeve and stirrer motor, air inlet, bottom thermometer and a distillation column with a column head and reflux divider, 170 g (1.3 mol) of 2-ethylhexyl alcohol, 455 g (4.55 mol) of methyl methacrylate (MMA), 0.129 g of hydroquinone monomethyl ether and 0.003 g of 4-hydroxy-2,2,6,6-tetramethylpiperidinyl-1-oxyl (inhibitors), and, as a catalyst, 80 g of the used catalyst from Example 1, were mixed. Subsequently, the mixture was stirred at a bottom temperature of 100° C. to 123° C. with introduction of air for 8 hours, in the course of which methanol and methyl methacrylate were distilled off. After the reaction had ended, the product was filtered through a fluted filter to remove the catalyst and freed of the MMA at 10 mbar.

The resulting yield of 2-ethylhexyl methacrylate was 156 g (60% based on the 2-ethylhexyl alcohol used). The purity of the product was 91.8% (determined by gas chromatography).

A portion of the product is bound adsorptively by the catalyst, which is appropriately reused in the next batch.

EXAMPLE 7

Example 7 was carried out in a manner essentially corresponding to Example 1, except that 62.5 g of Ambersep® 900 (Rohm & Haas Comp./USA) in the hydroxide form were used.

The resulting yield of 2-ethylhexyl methacrylate was 120 g (46% based on the 2-ethylhexyl alcohol used). The purity of the product was 93% (determined by gas chromatography).

A portion of the product is bound adsorptively by the catalyst, which is appropriately reused in the next batch.

EXAMPLE 8

100 g of ®Amberlyst A26 (Rohm & Haas Comp./USA) in the chloride form are charged into a chromatography column with the aid of demineralized water and admixed with 10% sodium carbonate solution until the effluxing eluate is chloride-free. Washing is then continued with demineralized water until the effluxing eluate is neutral. Washing is continued with methanol and the resulting ®Amberlyst A26 in the carbonate form is dried under air.

In a 1000 ml four-neck round-bottom flask equipped with a sabre stirrer with a stirrer sleeve and stirrer motor, air inlet, bottom thermometer and a distillation column with a column head and reflux divider, 170 g (1.3 mol) of 2-ethylhexyl alcohol, 455 g (4.55 mol) of methyl methacrylate (MMA), 0.129 g of hydroquinone monomethyl ether and 0.003 g of 4-hydroxy-2,2,6,6-tetramethylpiperidinyl-1-oxyl (inhibitors), and, as a catalyst, 62.5 g (10% by weight) of ®Amberlyst A26 (Rohm & Haas Comp./USA) in the carbonate form, were mixed. Subsequently, the mixture was stirred at a bottom temperature of 100° C. to 123° C. with introduction of air for 8.5 hours, in the course of which methanol and methyl methacrylate were distilled off. After the reaction had ended, the product was filtered through a fluted filter to remove the catalyst and freed of the MMA at 9 mbar.

The resulting yield of 2-ethylhexyl methacrylate was 125 g (48% based on the 2-ethylhexyl alcohol used). The purity of the product was 94% (determined by gas chromatography).

A portion of the product is bound adsorptively by the catalyst, which is appropriately reused in the next batch.

The invention claimed is:

1. A process for preparing a (meth)acrylic ester, the process comprising transesterifying a low-boiling ester of (meth) acrylic acid with a reactant alcohol in a reaction mixture in the presence of a catalyst, wherein the transesterifying is catalyzed by the catalyst, which is a basic ion exchanger, and wherein the transesterifying is effected at a temperature in a range from 70° C. to 120° C., wherein the basic ion exchanger is an anionic crosslinked styrene divinyl benzene copolymer containing quaternary ammonium groups, wherein the basic ions are hydroxide ions;

wherein the reactant alcohol is at least one monohydric or polyhydric alcohol selected from the group consisting of butanol, hexanol, 3 methylbutanol, heptanol, 2-ethylhexyl alcohol, 2 tert butylheptanol, octanol, 3 isopropylheptanol, nonanol, decanol, undecanol, 5 methylundecanol, dodecanol, 2 methyldodecanol, tridecanol, 5 methyltridecanol, tetradecanol, pentadecanol, hexadecanol, 2 methylhexadecanol, heptadecanol, 5 isopropylheptadecanol, 4 tert butyloctadecanol, 5 ethyloctadecanol, 3 isopropyloctadecanol, octadecanol, nonadecanol, eicosanol, cetyleicosanol, stearyleicosanol, docosanol, eicosyltetratriacontanol, ethylene glycol, trimethylolpropane, 1,2-propanediol, 1,3-propanediol, 1,3 butanediol, 1,4-butanediol, ethoxylated bisphenol A, 1,6-hexanediol, and pentaerythritol.

2. The process according to claim 1, wherein the basic ion exchanger is a strongly basic ion exchanger.

3. The process according to claim 1, wherein the low-boiling ester is at least one selected from the group consisting of methyl (meth)acrylate and ethyl (meth)acrylate.

4. The process according to claim 1, further comprising removing an alcohol released from the low-boiling ester of (meth)acrylic acid is by distillation.

5. The process according to claim 1, wherein the reactant alcohol is a monohydric alcohol.

6. The process according to claim 5, wherein the reactant alcohol is at least one selected from the group consisting of butanol, hexanol, 3 methylbutanol, heptanol, 2-ethylhexyl alcohol, 2 tert butylheptanol, octanol, 3 isopropylheptanol, nonanol, decanol, undecanol, 5 methylundecanol, dodecanol, 2 methyldodecanol, tridecanol, 5 methyltridecanol, tetradecanol, pentadecanol, hexadecanol, 2 methylhexadecanol, heptadecanol, 5 isopropylheptadecanol, 4 tert butyloctadecanol, 5 ethyloctadecanol, 3 isopropyloctadecanol, octadecanol, nonadecanol, eicosanol, cetyleicosanol, stearyleicosanol, docosanol, and eicosyltetratriacontanol.

7. The process according to claim 1, wherein the reactant alcohol is a polyhydric alcohol.

8. The process according to claim 7, wherein the reactant alcohol is at least one selected from the group consisting of ethylene glycol, trimethylolpropane, 1,2-propanediol, 1,3-propanediol, 1,3 butanediol, 1,4-butanediol, ethoxylated bisphenol A, 1,6-hexanediol, and pentaerythritol.

9. The process according to claim 1, wherein the reaction mixture comprises at most 0.5% by weight of water.

10. The process according to claim 9, wherein the reaction mixture comprises at most 0.05% by weight of water.

11. The process according to claim 1, wherein a molar ratio of low-boiling ester of (meth)acrylic acid to reactant alcohol present in the reaction mixture is increased during the transesterifying by at least 40% by adding low-boiling ester of (meth)acrylic acid.

12. The process according to claim 1, further comprising removing a mixture which comprises methyl methacrylate and methanol.

13. The process according to claim 1, further comprising adding methyl methacrylate during the transeserifying.

14. The process according to claim 1, wherein reaction time is in a range from 3 to 20 hours.

15. The process according to claim 1, wherein the basic ion exchanger comprises at least one selected from the group consisting of hydroxide ions and carbonate ions.

16. The process according to claim 1, wherein a weight ratio of the reactant alcohol to the low-boiling ester of (meth)acrylic acid is in a range from 2:1 to 1:10.

17. The process according to claim 1, wherein the transesterifying is effected at a pressure in a range from 200 to 2000 mbar.

18. The process according to claim 1, wherein the transesterifying is effected in the presence of a polymerization inhibitor.

19. The process according to claim 1, performed continuously.

20. A process according to claim 1, wherein a used basic ion exchanger, already employed in a prior transesterifying, is the catalyst.

21. The process according to claim 1, further comprising regenerating spent basic ion exchanger by treating the spent basic ion exchanger with an aqueous alkali metal hydroxide or carbonate solution.

* * * * *